United States Patent
Thiel et al.

(10) Patent No.: US 10,322,973 B2
(45) Date of Patent: Jun. 18, 2019

(54) POROUS SILICATE CERAMIC BODY, DENTAL RESTORATIONS AND METHOD FOR THE PRODUCTION THEREOF

(71) Applicant: VITA Zahnfabrik H. Rauter GmbH & Co. KG, Bad Sackingen (DE)

(72) Inventors: Norbert Thiel, Bad Sackingen (DE); Michael Dorn, Burladingen (DE); Joachim Bibus, Bad Sackingen (DE); Vilma Geske, Bad Sackingen (DE); Michael Tholey, Bad Sackingen (DE); Enno Bojemueller, Bad Sackingen (DE); Birgit Huber, Bad Sackingen (DE)

(73) Assignee: Vita Zahnfabrik H. Rauter GmbH & Co. KG, Bad Sackingen (DE)

( * ) Notice: Subject to any disclaimer, the term of this patent is extended or adjusted under 35 U.S.C. 154(b) by 38 days.

(21) Appl. No.: 14/469,828

(22) Filed: Aug. 27, 2014

(65) Prior Publication Data
US 2015/0050619 A1    Feb. 19, 2015

Related U.S. Application Data

(62) Division of application No. 14/079,676, filed on Nov. 14, 2013, which is a division of application No. (Continued)

(30) Foreign Application Priority Data

Jul. 21, 2008    (EP) .................................... 08160834
Oct. 28, 2008    (WO) ................. PCT/EP2008/064602
Mar. 31, 2009    (EP) .................................... 09156921

(51) Int. Cl.
C04B 35/16    (2006.01)
A61C 13/00    (2006.01)
(Continued)

(52) U.S. Cl.
CPC .......... *C04B 35/16* (2013.01); *A61C 13/0003* (2013.01); *A61C 13/0022* (2013.01);
(Continued)

(58) Field of Classification Search
CPC ......... C04B 35/16; C04B 35/64; C04B 38/00; A61C 13/0003; A61C 13/0022; A61C 13/083; A61C 13/20
See application file for complete search history.

(56) References Cited

U.S. PATENT DOCUMENTS 4,960,733 A    10/1990    Kasuga et al.
4,970,032 A    11/1990    Rotsaert
(Continued)

FOREIGN PATENT DOCUMENTS

EP    0631995    1/1995
EP    0870479    10/1998
(Continued)

*Primary Examiner* — John E Uselding
(74) *Attorney, Agent, or Firm* — Jacobson Holman PLLC

(57) ABSTRACT

A porous, silicate, ceramic body, optionally with different colors, with a first density, can be sintered into a silicate, ceramic body with a second density, wherein the ratio of the first density to the second density is 2/5 to 98/100, and the three-point bending strength of the porous, silicate ceramic body with a first density, measured according to ISO 6872, is 25 to 180 MPa.

7 Claims, 4 Drawing Sheets

Related U.S. Application Data

12/737,491, filed as application No. PCT/EP2009/059359 on Jul. 21, 2009, now abandoned.

(51) Int. Cl.
*A61C 13/083* (2006.01)
*A61C 13/20* (2006.01)
*C04B 38/00* (2006.01)
*C04B 35/64* (2006.01)
*C04B 111/00* (2006.01)

(52) U.S. Cl.
CPC ............ *A61C 13/083* (2013.01); *A61C 13/20* (2013.01); *C04B 35/64* (2013.01); *C04B 38/00* (2013.01); *C04B 2111/00836* (2013.01); *C04B 2235/6022* (2013.01); *C04B 2235/6026* (2013.01); *C04B 2235/656* (2013.01); *C04B 2235/6562* (2013.01); *C04B 2235/6567* (2013.01); *C04B 2235/6581* (2013.01); *C04B 2235/661* (2013.01); *C04B 2235/77* (2013.01); *C04B 2235/96* (2013.01); *C04B 2235/9607* (2013.01); *C04B 2235/9615* (2013.01); *C04B 2235/9661* (2013.01)

(56) References Cited

U.S. PATENT DOCUMENTS

| | | | |
|---|---|---|---|
| 5,106,303 A | 4/1992 | Oden et al. | |
| 5,314,335 A * | 5/1994 | Fung | A61C 13/0003 433/223 |
| 5,614,330 A | 3/1997 | Panzera et al. | |
| 5,775,912 A | 7/1998 | Panzera et al. | |
| 5,849,068 A | 12/1998 | Hofmann et al. | |
| 5,916,498 A | 6/1999 | Hofmann et al. | |
| 5,944,884 A * | 8/1999 | Panzera | C03C 4/0021 433/202.1 |
| 6,126,732 A | 10/2000 | Hofmann et al. | |
| 6,354,836 B1 | 3/2002 | Panzera et al. | |
| 6,455,451 B1 | 9/2002 | Brodkin et al. | |
| 6,554,615 B1 | 4/2003 | Brodkin et al. | |
| 6,706,654 B2 | 3/2004 | van der Sel | |
| 6,802,894 B2 | 10/2004 | Brodkin et al. | |
| 7,091,142 B2 | 8/2006 | Assmann et al. | |
| 7,294,392 B2 | 11/2007 | Aechtner et al. | |
| 2002/0198093 A1 | 12/2002 | Van der Zel | |
| 2004/0081847 A1 | 4/2004 | Aechtner et al. | |
| 2004/0121894 A1 | 6/2004 | Brodkin | |
| 2004/0137399 A1 | 7/2004 | Freischfresser | |
| 2004/0232576 A1 | 11/2004 | Brodkin et al. | |
| 2006/0082033 A1 | 4/2006 | Hauptmann et al. | |
| 2006/0105297 A1 * | 5/2006 | Knapp | A61C 13/09 433/206 |
| 2007/0056467 A1 | 3/2007 | Panzera et al. | |
| 2010/0221682 A1 | 9/2010 | Burger et al. | |

FOREIGN PATENT DOCUMENTS

| | | | |
|---|---|---|---|
| EP | 1253116 | 10/2002 | |
| JP | 1-145064 | 7/1989 | |
| JP | 1992-505113 | 6/1994 | |
| JP | H07-23986 | 1/1995 | |
| JP | 08-119669 | 5/1996 | |
| JP | 11-314938 | 11/1999 | |
| JP | 2003012384 | 1/2003 | |
| JP | 2003-048770 | 2/2003 | |
| WO | 02/09612 | 2/2002 | |
| WO | WO-2009052082 A2 * | 4/2009 | ........... A61C 13/082 |

\* cited by examiner

POROUS SILICATE CERAMIC BODY, DENTAL RESTORATIONS AND METHOD FOR THE PRODUCTION THEREOF

This is a divisional of Ser. No. 14/079,676, filed Nov. 14, 2013, which is a divisional of Ser. No. 12/737,491, filed Apr. 12, 2011, which is a 371 of PCT/EP09/59359, filed Jul. 21, 2009, and which has priority of EP 08160834.1 filed Jul. 21, 2008, EP PCT/EP08,064602, filed Oct. 28, 2008, and EP 09156921.0, filed Mar. 31, 2009, the disclosures of which are incorporated herewith by reference.

The present invention relates to a porous silicate-ceramic body, a dental restoration precursor, a dental restoration, a process for preparing a porous silicate-ceramic body, a process for preparing a dental restoration, and the use of the porous silicate-ceramic body according to the invention.

In the dental industry, a distinction is generally made in the CAD/CAM field between two different groups of applications for molded members, such as blocks, disks etc.: ceramics for scaffold structures to be ceramic-fused, and ceramics or glass ceramics for the so-called chair-side application, i.e., blocks from which the dentist can grind a restoration for the patient in one visit with them, which restoration can be cemented in place in the same visit after having been completed and individualized. The scaffold materials are dense or porous ceramic blocks, wherein the scaffolds made of the porous ceramics get their final shape and strength by a sintering or glass infiltration process. The ceramics for the chair-side application are dense ceramic or glass-ceramic blocks, which must be aftertreated merely mechanically (polished) after a grinding or milling process, or subjected to a short firing process to achieve the final strength (crystallization firing) or surface finish (so-called glaze firing).

U.S. Pat. No. 5,106,303 describes a porous block from which a restoration, for example, a veneer, can be prepared by grinding or milling. The described block consists of oxide ceramics, such as stabilized $ZrO_2$ or $Al_2O_3$. The restoration is ground from the porous block with an enlargement factor, which is not specified, and subsequently dense-sintered. Among others, there is a drawback in that the restoration must be ceramic-fused subsequently.

U.S. Pat. No. 5,775,912 describes the preparation of a restoration from a porous block of feldspar or veneer ceramic material by means of CAD/CAM technology. The theoretical density of the block is less than 85% of the density after the dense-sintering. However, the disadvantage of the method described is the fact that an enlargement factor is not integrated in the grinding process and the material remains to be ceramic-fused after the dense-sintering. In addition, it is described that the porous structure must be supported on a refractory, highly temperature-resistant material during the dense-sintering.

U.S. Pat. No. 6,354,836 describes a porous block from which a desired restoration can be ground to an enlarged size, but close to the final contours, and must be dense-sintered afterwards. The block consists of $ZrO_2$, $Al_2O_3$, general oxide ceramics or glass ceramics. The disadvantage of the process described is that the block exhibits isotropic shrinkage, i.e., equal shrinkage in all three directions in space, during sintering. In addition, oxide ceramics generally still must be ceramic-fused, as in the case of $ZrO_2$ and $Al_2O_3$.

U.S. Pat. No. 6,106,747 describes a process for supporting porous structures during dense-sintering. This involves the preparation of a support structure, preferably from the same material as the porous restoration to be sintered, which has the same shrinkage during sintering. The porous restoration is rested on this structure during sintering. The porous structure may have been ground from blocks, oxide ceramic blocks, or consist of materials applied from a suspension or slip, such as oxide materials for glass infiltration or feldspar materials. The disadvantage of this process is that the remnants of the support structure must be removed after the dense-sintering, and that the surfaces of the restoration may be attacked during such removal. Therefore, a material for dense-sintering that does not require a form-stabilizing support is more advantageous.

The advantage of the ceramics for the chair-side process is the fact that the patient is quickly provided with an aesthetically demanding crown. The disadvantage resides in the processing. Since these materials are very solid because they are dense, i.e., hardly or not at all porous, the grinding process involves a significant expenditure of time. In addition, the grinding devices or milling machines wear away very quickly due to the relatively high hardness, and there is a risk that small pieces may break out/off, also referred to as "chipping", particularly in thin marginal regions of the restoration.

The aftertreatment of the restoration surface, i.e., removal of the grinding marks and polishing of the surfaces to achieve a tooth-like gloss, also requires a significant expenditure of time, and the instruments for polishing are also subject to a great wear.

Thus, one object of the invention is to provide a body that avoids the drawbacks mentioned. Another object is to provide a process for preparing such a body.

The object of the invention is achieved by a porous silicate-ceramic body, optionally with different colors, having a first density that can be sintered to a silicate-ceramic body having a second density, wherein the ratio of the first density to the second density is from 2/5 to 98/100, especially from 12 to 98/100, and the three-point bending strength of said porous silicate-ceramic body having a first density as measured according to ISO 6872 is from 25 to 180 MPa.

Figure 1:
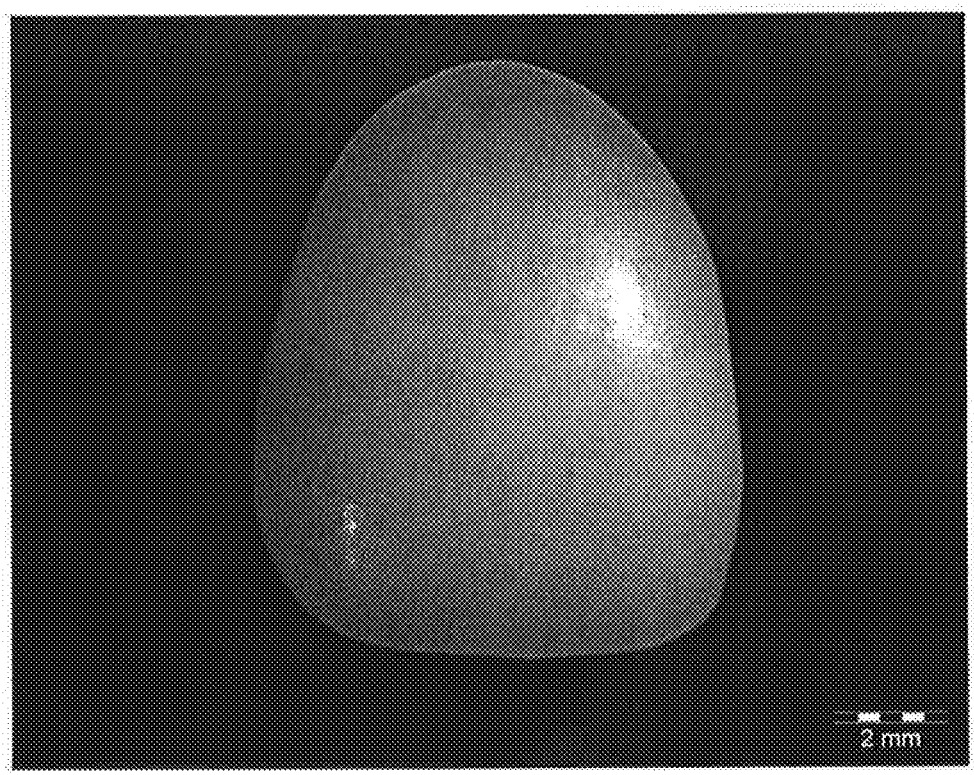
FIG. 1 is a photograph of the front view of a crown prepared from a porous silicate body.

In a particular embodiment of the invention, the second density of the porous silicate-ceramic body according to the invention approximately corresponds to the theoretically reachable density of the ceramic body.

The desired density of the porous molded member is defined by the material (chemical properties) and the grinding or milling parameters of the machine to be employed (physical parameters). Depending on the grinding or milling system, the molded member must be adjusted to a particular density range in order to ensure a non-damaging processing. The reaching of the block density is controlled by the sintering time and the sintering temperature.

Generally, a reduction of the sintering temperature causes an extension of the sintering time, and an increase of the sintering temperature causes a shortening of the sintering time.

The porous structure of the silicate-ceramic body enables a quicker grinding or milling with less wear to the tool used for material removal. Due to the easier processing, the chipping of material from the restoration can be prevented.

In addition, the surfaces can be smoothed by a sintering step taking place after the grinding, i.e., any grinding marks are substantially or completely removed. The tedious polishing of the dense surfaces can be omitted, but it is possible to polish or smooth the surface in the porous state. In addition, the above mentioned firing for surface finishing, the so-called glaze firing, can be omitted because of the sintering step.

Another advantage of the porous silicate-ceramic body according to the invention can be seen in the fact that objects shapeable from the body can be employed as veneer materials (also referred to as veneers in the following) in dental technology for preparing dental prostheses. It is understood by one skilled in the art that the coefficient of thermal expansion (CTE) of the porous silicate-ceramic body is adjusted, especially for use as a veneer material for a scaffold. The CTE as measured according to ISO 6872 is to be, for example, at least $7 \times 10^{-6}$ $K^{-1}$, especially from 7 to $18 \times 10^{-6}$ $K^{-1}$.

If the scaffold to be ceramic-fused is made of metal, for example, of a gold alloy or a base metal, the CTE of the porous silicate-ceramic body according to the invention as measured according to ISO 6872 should typically be from 7 to $16 \times 10^{-6} K^{-1}$, especially from 12 to $15 \times 10^{-6}$ $K^{-1}$.

Metal alloys that can be used for veneer ceramics and their CTE values are generally published by the manufacturers of veneer ceramics and are known to the skilled person. Preferably, the CTE of the dental ceramics is selected to be lower, for example, by 0.5 to several units, than that of the scaffold material in order to build up a compression stress within the restoration.

The porous silicate-ceramic body according to the invention may also be applied to ceramic scaffolds for fusing. In this case, it is recommended to select the CTE of the body as measured according to ISO 6872 to be from 7 to $11 \times 10^{-6}$ $K^{-1}$ provided that the CTE of the scaffold material is within this range.

| Scaffold ceramics | CTE $[10^{-6} K^{-1}]$ |
| --- | --- |
| Y-TZP ($ZrO_2$) | ~9 |
| $Al_2O_3$ | ~7 |
| In-Ceram alumina | ~7 |
| In-Ceram zirconia | ~7 |
| In-Ceram spinel | ~7 |

The three latter materials in the Table are glass infiltration ceramics.

In most cases, it may be indicated to select the colors of the porous silicate-ceramic body according to the invention that as natural an appearance of the veneer as possible and thus the result of a dental restoration is obtained. For this purpose, the block may be composed, for example, of layers having different translucencies and/or colors. Another possibility is the introduction of a three-dimensional structure as described in the application PCT/EP2008/064602, which enables the course of the enamel line of a human tooth to be imitated in a way substantially true to nature. The subject matter of this application is included herein by reference.

This patent application discloses a molded member made of form-stabilized material comprising at least a first component and a second component, characterized in that said second component has a different color from that of the first component, and the second component is arranged within the first component to form an interface in such a way that said interface represents a surface curved in space.

In one embodiment, the molded member is designed in such a way that the interface at least partially corresponds to the course of the dentin/enamel border of natural or artificial teeth. The colors of the first component and second component are selected so as to come as close as possible to the enamel or dentin color of a natural tooth or artificial tooth. Thus, it becomes possible to provide for a wide variety of courses of the dentin/enamel borders of teeth in the molded member, so that an individual adjustment of the border lines in a dental restoration to be prepared can be effected.

The shape of a molded member can be stabilized by different measures. In particular, this can be achieved by mechanical action, especially by pressure, typically within a range of 5-500 MPa, for example, by pressing. Further shaping methods are known to the skilled person. In addition, additive methods, for example, injection molding, may be used for the preparation.

The colors of the components of the molded member according to the invention can be achieved by pigmentation, in the simplest case by means of color pigments, which may at the same time also serve to adjust the translucency. The translucency may also be adjusted by opaquers.

For the use of the molded member according to the invention in dental technology, those molded members whose first and second components are ceramic materials, especially feldspar or oxide ceramic materials, are particularly suitable. However, it is also possible to employ a plastic material. The plastic material may be a thermoplastic material or a thermosetting material. An acrylate-based plastic material is particularly suitable. Suitable plastic materials are known to the skilled person and typically include those used in the preparation of artificial teeth.

First and second components of feldspar ceramic materials comprising metal oxides selected from the group consisting of $SiO_2$, $Al_2O_3$, $Na_2O$, $K_2O$, optionally supplemented by adding pigments and inorganic fillers, may also be used.

In another embodiment, the components may consist of oxide ceramic materials comprising metal oxides selected from the group consisting of $SiO_2$, $Al_2O_3$, $ZrO_2$ stabilized by various compounds ($Y_2O_3$, $CeO_2$ etc.), optionally supplemented by adding pigments or compounds of colored ions.

In another embodiment of the invention, the molded member according to the invention contains a binder for improving the dimensional stability, especially of the sinterable material. For example, a binder that can be employed is selected from the group consisting of acrylate(s), polyvinyl alcohol (PVA), polyvinyl acetate (PVAC), polysaccharide/acrylic acid (PS/AC), cellulose derivatives or mixtures thereof. Additional auxiliaries, such as water, lubricants for reducing the friction, sintering aids for accelerating the densification, or dispersants, plasticizers, wetting agents and thermoplasts for affecting the rheological properties may be added.

In a particularly preferred embodiment, the interface between the first and second components of the molded member, i.e., especially the interface between the material imitating the dentin of a tooth and that imitating the enamel, is essentially described by a family of parabolas. Parallel cross-sectional planes through the molded member can be laid into the molded member in such a way that the boundary between the two components appears as a parabolic border line. In this case, the border line is parabolic through at least ⅔, especially ¾, of its length. Especially the margins or ends of the border line may have a shape differing from that of a parabola, wherein this region of the border line too preferably has no leap or step. In particular, the parabolic border line becomes flatter in the marginal region and is preferably outward oriented.

Over a width of the molded member extending perpendicular to the parallel cross-sectional planes, at least 70% of the cross-sectional planes, especially at least 80% of the cross-sectional planes, have a parabolic border line as defined above.

In an orientation of the molded members in which the second component, i.e., especially the material imitating the dentin, is arranged in the lower portion of the molded member, the parabolas forming the border lines are open towards the bottom. This generates maximums, wherein in a preferred embodiment the parabolas are mirror-symmetrical to a plane extending through the maximums. If the molded member is arranged in this way with dentin facing downward, a plane of symmetry can thus be drawn through all the maximums of the parabolas in a preferred embodiment.

In a preferred embodiment, a major cross-sectional plane can be defined which in the position of the molded member with dentin facing downward is the cross-sectional plane in which the parabolic border line has the greatest or highest maximum. Starting from the major cross-sectional plane, the height of the border line preferably decreases continuously in a taper direction. In particular, a curve defined by the maximums decreases continuously at least through a major part of its length of especially more than half and preferably more than ¾ of its length. The connecting curve of the maximums preferably lies in the plane of symmetry and/or is oriented perpendicular to the major cross-sectional plane. Relative to the width of the second component in the taper direction, the decrease of the maximums of the parabola preferably goes through at least 50%, more preferably through at least 75%, of the total length or total width of the second component.

Preferably, both ends of the border line or both ends of the branches of the parabola merge into a curve of opposite curvature. Thus, in a preferred embodiment, the parabolic part of the border line is followed by an outward curve to form a point of inflection.

The above described particularly preferred embodiment of the interface between the first component, which imitates the enamel, in particular, and the second component, which imitates the dentin, in particular, may have slight deviations. This is a geometric approximation, so that deviations of up to 10% are possible. In particular, the design of the border line is effected on the basis of experience and of examinations of the enamel/dentin border in natural and/or artificial teeth.

For preparing an artificial tooth, the molded member can preferably be represented by a suitable computer software and can rotate freely in space, in particular. Thus, a dentist or dental technician can view the border line from different perspectives. The geometric dimensions of the tooth to be reproduced are transmitted to the computer, for example, by image processing programs. The dentist or dental technician can arrange the virtual tooth produced thereby in any position desired within the molded member and thus arrange the interface between the dentin and enamel in such a way that the appearance of impression of the tooth to be prepared later from the molded member corresponds to that of the patient's natural teeth, especially the patient's neighboring teeth, or is at least very similar.

The process according to the invention may serve for preparing the molded member according to the invention consisting of a sinterable material, which has at least one first and at least one second component, wherein
a) said at least one first component is filled into a mold;
b) a depression having a surface is pressed into the filled-in at least one first component of said material, especially sinterable material or plastic material; and
c) said surface forms an interface curved in space towards
d) the at least one second component filled into the depression.

The surface of the interface is designed to correspond at least partially to the course of the dentin/enamel border of natural or artificial teeth.

The preparation of the molded member may also be effected by ceramic injection molding or similar preparation methods.

According to one embodiment of the invention, the construction of the interface is effected by positioning the enamel/dentin interfaces of different natural and/or artificial teeth. In natural teeth, the enamel can be carefully removed in a preparative manner to characterize the position of the interface between the enamel and dentin. In doing so, it is to be taken care that the dentin layer is not ablated. It is easier to prepare artificial teeth and the course of their interface. The course of the interface in artificial teeth mimics the course in natural teeth. In order to prepare members showing this course of the interface, the teeth are not prepared with all the layers, but the more translucent enamel layer is omitted. Thus, after the sintering process, a surface of the artificial tooth is obtained that corresponds to the course of the enamel/dentin interface.

By preparing different teeth, a curved surface corresponding to the course of the interface of the different teeth can be modeled by arranging the different dentin/enamel interfaces in space, preferably by a size-dependent arrangement. From this model, a mold can be prepared.

An alternative possibility of modeling the interface is to digitalize courses of the enamel/dentin interface and to generate the model by a software. This offers the possibility to include a substantially higher number of interface courses in the generation of the interface. In addition, a mold can then be prepared much more easily by means of CAD-CAM methods.

Using the mold, a desired molded member can be prepared. In order to effect a three-dimensional measurement of the molded member or the course of the interface, a molded member is sawed into as large as possible a number of plane-parallel disks, and the disks are ground smooth on both sides. Before the sawing, a continuous mark, preferably a groove, that connects diagonal corners of the molded member is applied to the molded member perpendicular to the sawing direction, enabling an unambiguous determination of the position of a disk by measuring the position of the groove on the edge of the disk.

By measuring the position of the interface on the disks, a point cloud representing the enamel/dentin interface can be established in a coordinate system.

The process described therein may involve a sintering step as an intermediate step. This has the advantage that the molded member is more stable.

The molded member according to the invention may also be prepared by correspondingly performed dry or wet processes, such as pressure slip casting.

For example, the preparation process by means of pressure slip casting can be performed as follows:
a.) preparing a molded member A having the geometry of the surface from the above mentioned preparation process by casting a slip, for example, into a porous plaster mold whose surface corresponds to the boundary described, with or without application of pressure;

b.) preparing a second molded member B with a negative contour with respect to molded member A according to a.);

c.) assembling the two molded parts A and B into a compound unit C, possibly with thermal aftertreatment, with or without pressure within or outside a mold (after demolding) that determines the overall outer shape of compound unit C (surface of the assembled component/compound unit).

Or:

a.) preparing a molded member A having the geometry of the surface from the above mentioned preparation process by casting a slip, for example, into a porous plaster mold whose surface corresponds to the boundary described, with or without application of pressure;

b.) demolding molded member A and positioning molded member A in another plaster mold that is to correspond to the final contour of the compound unit;

c.) filling the mold with another slip with or without application of pressure and possibly with thermal aftertreatment within the mold or after demolding.

The preparation process by means of a dry process can be performed as follows:

a.) preparing a molded member A having the geometry of the surface from the above mentioned preparation process by inserting a plasticized composition with or without added binders into a corresponding mold, possibly with thermal stabilization with or without pressure;

b.) preparing a second molded member B with a negative contour with respect to molded member A according to a.);

c.) assembling the two molded parts A and B into a compound unit C, possibly with thermal aftertreatment, with or without pressure within or outside a mold that determines the overall outer shape of compound unit C (surface of the assembled component/compound unit).

The preparation processes described have long been known in principle in the field of ceramic forming (Hülsenberg, Keramikformgebung, ISBN 3-342-00098-8).

The molded member can be employed for preparing a dental restoration, which is constructed and prepared, in particular, by CAD/CAM methods.

The invention also relates to a process for preparing a molded member made of form-stabilized material with an interface extending within the molded member, wherein said material has at least a first component and a second component;

said second component has a pigmentation different from that of the first component, and the second component is arranged within the first component to form an interface in such a way that said interface represents a surface curved in space;

said interface is obtainable by creating surfaces having radii of curvature with different degrees of curvature from sections made through a set of natural or artificial teeth; and/or said interface is obtainable by creating surfaces having radii of curvature with different degrees of curvature from courses of the dentin/enamel border of natural or artificial teeth of the set;

the created surfaces having radii of curvature with different degrees of curvature are arranged in space as a function of the degree of curvature of the radii of curvature; and wherein an arrangement in space of the created surfaces resulting therefrom produces the totality of the interface.

In one embodiment of the process described in the international application for preparing the molded member according to the invention with the interface, the marginal region of the courses of the dentin/enamel border can be left unconsidered when the created surfaces are arranged.

In another embodiment, the production of the totality of the interface can consider only those teeth whose dentin/enamel border is in accordance with a predetermined approximating surface to at least 80%, especially at least 90%. In particular, the approximating surface is approximated by significant dentin/enamel borders of natural or artificial teeth.

In still another embodiment of the process according to the invention, the teeth having a great curvature of the dentin/enamel border are combined to form an apical region of the interface, or arranged in the apical region of an approximating surface. For example, the teeth selected to be arranged in the apical region can be sorted essentially by their size.

In another embodiment of the process according to the invention, the teeth having a small curvature of the dentin/enamel border are combined in the marginal region of the interface, or arranged in the marginal region of an approximating surface. In this case too, the teeth selected to be arranged in the marginal region can be sorted essentially by their size.

In another embodiment of the process according to the invention, the teeth having a medium curvature of the dentin/enamel border may be combined to form an intermediate region of the interface arranged between the marginal region and the apical region, or arranged in the intermediate region of an approximating surface. In this case too, the teeth selected to be arranged in the intermediate region can be sorted essentially by their size.

According to the invention, it is also possible to perform the size sorting in the same direction in space independently of the intensity of the curvature.

In order to facilitate the processing of the porous silicate-ceramic body according to the invention, especially by CAD/CAM processing methods, the porous silicate-ceramic body is designed as a molded member. For example, this porous silicate-ceramic body according to the invention has a holding element as described, for example, in DE-A-103 22 762, or as usually employed today for the various CAD/CAM and/or copy-grinding systems, depending on the manufacturer. In this case, the holding element is adhesive-bonded to the body, or else the shape of the body already has a corresponding holding element, for example, a groove, due to its preparation process.

In another embodiment, the porous silicate-ceramic body according to the invention may be arranged in a matrix for embedding. This also facilitates or enables the processing, especially mechanical processing, in a CAD/CAM machine and/or in a copy-grinding system for processing. For example, the Everest® system from KaVo, Biberach, Germany, has already been known.

Therefore, the present invention also relates to a dental restoration precursor obtainable by processing the porous silicate-ceramic body according to the invention.

After the determination of the sintering shrinkage or the so-called enlargement factor (the enlargement factor is an equivalent of the shrinkage factor and corresponds to the factor by which a workpiece ground from a molded member must be enlarged for the workpiece to have the desired size after dense-sintering, both being determined in a direction-dependent way in general), a dental restoration precursor can be ground from the porous silicate-ceramic body. Since the dental restoration is ground from the molded member with a defined enlargement, the dense dental restoration obtains the desired size and shape.

The present invention further relates to a dental restoration that can be prepared therefrom, obtainable by dense-sintering the dental restoration precursor, considering the sintering shrinkage if necessary, in order to apply the restoration to a prepared object, for example, a tooth stump in a patient.

The dense-sintering of the dental restoration precursor is effected, for example, in a commercially available furnace for veneering dental restorations. As with veneering, it is recommended that a vacuum be applied during sintering as well. The sintering temperature and sintering time are to be matched to the silicate-ceramic material and its physical properties and the desired surface properties of the dental restoration.

According to the invention, a dental restoration precursor obtainable by processing the porous silicate-ceramic body according to the invention and applying it to a complementary scaffold can also be prepared. This dental restoration precursor is also referred to as a "porous veneer" in the following.

If the CTE of the silicate-ceramic molded member is adjusted to the CTE of a scaffold material, a superstructure can be ground from the porous silicate-ceramic molded member by means of CAD/CAM methods or other grinding or milling methods, said superstructure being applied to the scaffold and subsequently sintered onto the scaffold as described above. Rather than the tooth stump or the model of the tooth stump, the surface of the scaffold structure serves as the basis for the grinding/milling of the structure from the porous molded member.

It is recommendable to take care that the scaffold has no or only very little undercuts on the surface to which the dental restoration precursor is applied as a porous veneer. When the veneer is later applied to the scaffold, undercuts may cause problems due to the decreasing diameters. In addition, cavities form during dense-sintering, which may lead to stresses and cracks.

When the scaffold and veneer is constructed, it is advantageous to construct the interface of the scaffold in such a way that the veneer has to be placed on the scaffold in an unambiguous position and without the possibility of inadvertent displacement.

Another possibility of exact positioning and ensuring as accurate a bonding as possible is to design the veneer during its construction in such a way that the interface between the veneer and the scaffold is congruent, that is the inner surface of the veneer is ground to fit onto the outer surface of the scaffold rather than to be enlarged, and the outer surface of the veneer is ground to an enlarged size in accordance with the density or taking a shrinkage factor into account. Further, the inner surface of the veneer can be ground to be larger than congruent to maximally smaller than the inner surface of the veneer that results from a calculation with the previously measured enlargement factor of the block, while the outer surface of the veneer is ground to an enlarged size in accordance with the density or taking a corresponding shrinkage factor into account. This means that the inner surface of the restoration is ground with a smaller enlargement factor that the previously determined enlargement factor of the porous block, which represents the maximum enlargement factor with which a veneer can still be ground and dense-sintered to conform exactly to the scaffold after sintering. Depending on the enlargement factor applied to the inner side, an enlargement factor for the outer side is calculated that is based, among others, on the calculated enlargement factor of the block, but also takes the non-maximum enlargement factor of the inner side into account.

If required by the corresponding restoration, a dental restoration obtainable by dense-sintering the dental restoration precursor according to the invention may also be provided according to the invention. It may then be arranged on a complementary scaffold, taking a sintering shrinkage into account if necessary.

The bonding between the veneer and the scaffold can be realized by sintering the veneer, adhesive bonding with commercially available dental adhesives, or by using a solder, preferably a glass solder, as described in WO-A-2006/120255 A.

The present invention also relates to a process for preparing the porous silicate-ceramic body according to the invention, wherein the production of the green body can be effected by per se known preparation processes with powders or granules in ceramic shaping (see also Hülsenberg, Keramikformgebung, ISBN 3-342-00098-8). These include, for example:

Slip pressure casting
dry pressing of granules
extruding or the like.

In contrast to preparation processes for glass-ceramic dental molded members according to the prior art, the preparation process according to the invention may be understood as a sintering process interrupted before complete dense-sintering, to form a porous body.

The present invention also relates to a process for preparing dental restorations according to the invention, comprising the steps of:

processing the porous silicate-ceramic body according to the invention, followed by
a) positioning the veneer on a scaffold and subjecting it to sinter firing; or
b) dense-sintering the restoration precursor into the final dental restoration; or
c) dense-sintering the veneer followed by positioning and bonding (by sintering, adhesive bonding, using a glass solder) to a scaffold.

The invention will be further illustrated by the following Examples, which do not limit the subject matter of the invention.

The grinding machine used for the experiments was a Sirona inLab machine. By the selection of the machine and its grinding parameters, the parameters of the molded members to be prepared were defined since a positive result can be achieved with the predetermined grinding parameters only for defined block parameters.

The basis of the test specimens was a mixture of feldspar ceramics. The feldspar granules were shaped and pressed. The molded member obtained therefrom was freed from binder in accordance with the additives used in the granules according to the prior art, followed by porous-sintering at a temperature of 1125° C. After the removal of the binder, the molded members were sintered directly, that is while still hot, or after being preheated in a furnace under vacuum. The sintering time was selected to reach a density of the porous body of above 85% to 95% of the theoretical density of the dense material at a predetermined temperature. The heating rate was a few minutes after reaching the target temperature in order to prevent flowing. The molded member was removed from the furnace while hot.

To determine the shrinkage/enlargement factor, porous bodies were measured, dense-sintered and again measured. With the sintering shrinkage thus defined in three directions in space, and after fixtures were attached, crowns were ground from the porous bodies by means of Sirona inLab. These crowns were dense-sintered under vacuum at a temperature of 1165° C.:

preheating at 600° C. for 6 min before the restoration was placed in the furnace;

heating to the final temperature (1165° C.) for 40 min;

maintaining at maximum temperature for 10 min.

There was a vacuum during the heating and during the sintering.

The furnace was opened at the maximum temperature, and the restoration cooled down in the air, or else the restoration was slowly cooled in the closed or slightly opened furnace.

Figure 2:
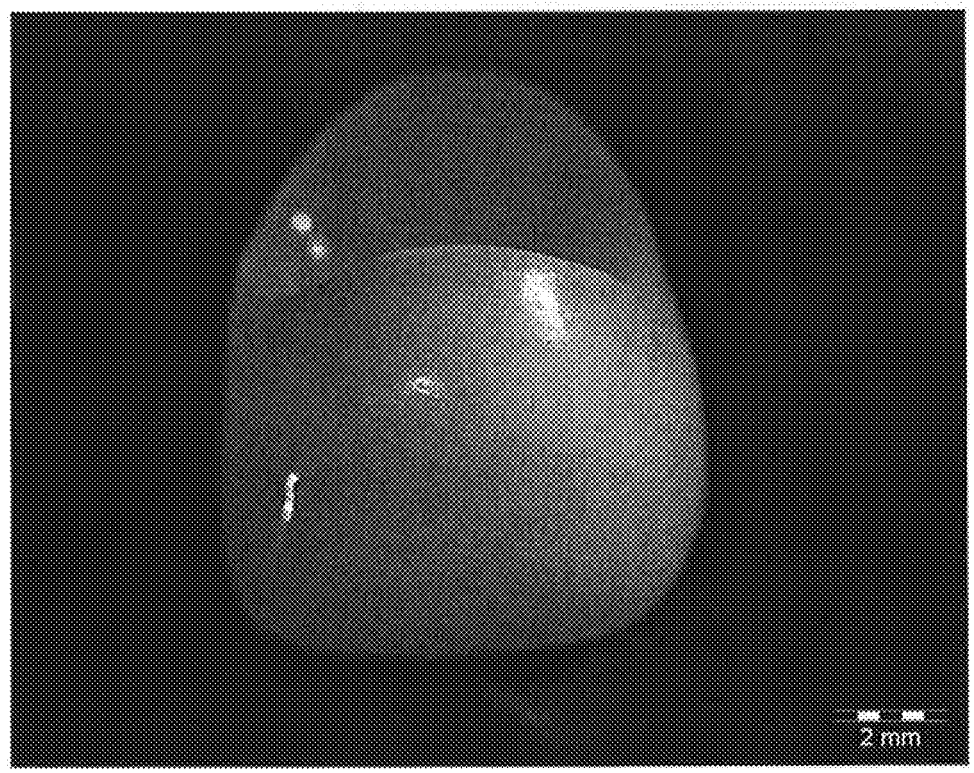
FIG. 2 is a photograph of the rear view of a crown prepared from a porous silicate body.
Figure 3:
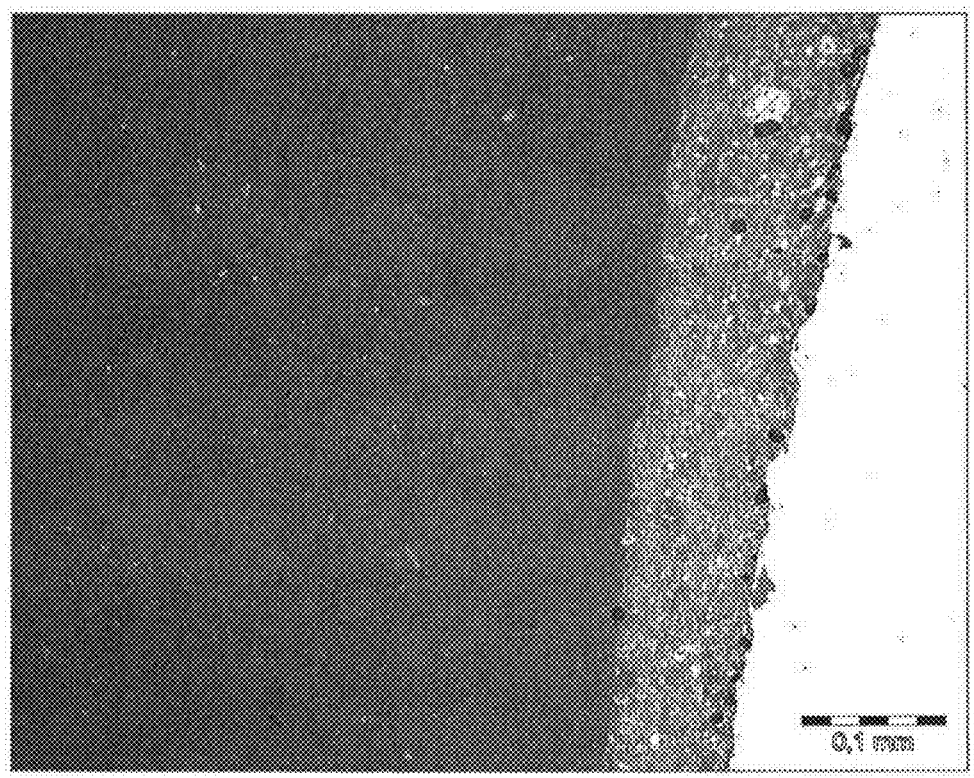
FIG. 3 is a photograph of a section of a base metal crown with a VM13 veneer.
Figure 4:
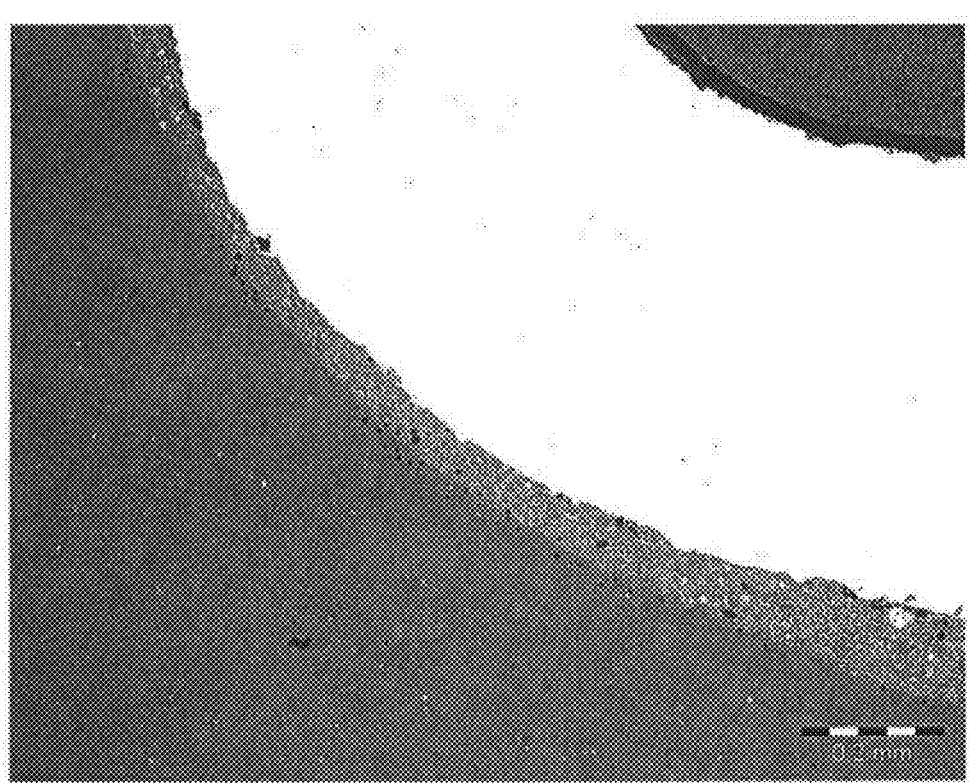
FIG. 4 is a photograph of a section of a base metal crown with a V13 veneer.

FIGS. 1 and 2 shows photographs of a crown prepared from a porous silicate-ceramic body. FIG. 1 shows a crown prepared from a porous feldspar block and dense-sintered: front view. FIG. 2 shows a crown prepared from porous feldspar block and dense-sintered: rear view. FIG. 3 shows a section of the composite of a base metal crown with a VM13 veneer ground from a molded member. The left side of the photograph shows the dense veneer. The intermediate is an opaquer, and the white region on the right side is the base metal scaffold. FIG. 4 shows a section of the composite of a base metal crown with a V13 veneer ground from a molded member. What can be seen in the ground section is the base metal crown (white), the applied opaquer (light gray) and the dense veneer (dark gray, left).

It was found that when a higher sintering temperature was used for the same sintering time, the density of the molded member became so high that no restoration could be ground with the predetermined grinding parameters. There was chipping, and the CAM/CAD machine in part aborted the grinding processes because of too high load on the grinding disk.

Molded members presintered without a vacuum could not be used since inclusions in the ceramics caused it to become turbid. The lowering of the heating rate during the porous-sintering caused the bodies to flow, whereby regions with different densities were produced in the bodies. Thus, an accurate processing was not possible.

Veneers for zirconium dioxide caps were also prepared from the above mentioned molded members. For this purpose, the dense-sintered caps were scanned in by means of a commercially available CAD/CAM system, and a fully anatomic design of the veneer was performed. After the veneer had been ground out, it was sintered onto the zirconium dioxide cap. For this process, the same sintering program was used as for the dense-sintering of a full crown (see above).

When attaching by sintering, it is advantageous that the veneer does not slip when positioned in the furnace. It is advantageous if the surface of the ceramic scaffold and the inner side of the veneer are designed accordingly. Grinding geometries already integrated in the software are particularly recommendable.

Advantageously, no or only very small undercuts should be constructed when the scaffold construction is designed. The defined sintering shrinkage of the molded members or the ground porous constructions enables no or only a very slight additional shrinkage. An additional shrinkage would not be achieved by the porous structure, but by the surface tension of the object and the natural property of liquid and viscous bodies to reach as small a surface as possible. However, this may lead to stresses and cracks, since the molded member shrinks to different extents.

Further, porous molded members that were processed into veneers were prepared from leucite-reinforced commercially available veneer ceramic powders (Vita VM9 and VM13 veneer ceramics). The veneer ceramic powders matched to the respective CTE of the scaffold material were shaped by simple pressing. Optionally, a binder or other additives for shaping can be used for a better handling.

The CTE of the veneer ceramics was within a range of from 9 to 13.

For the preparation of molded members having a CTE of 9, the veneer ceramic powder was shaped and sintered. The sintering was performed without preheating and under vacuum throughout the sintering process. The blocks were placed into a furnace preheated at 500° C. to 600° C. In 10 min, they were heated to a temperature of 780° C. and then maintained at this maximum temperature for 5 min. The following Table shows different experiments with the respective properties:

| Maximum temperature [° C.] | Remarks |
|---|---|
| 700 | The block is too soft |
| 750 | The block can just be used, but is not very solid |
| 780 | The block has ideal properties for the predetermined grinding program, no chipping during the grinding |
| 800 | The block is readily ground. |

It was found that the molded members sintered below 750° C. were too soft. With increasing temperature, the processing properties for the Sirona grinding machine improved.

The ground ceramic veneers were fired onto zirconium dioxide caps with the following sintering program:

preheat at 500° C. for 6 min heat at 910° C. with 55° C./min hold the maximum temperature for 1 min The temperature program employed corresponds to the normal firing program for this veneer ceramics.

The preparation of the molded members having a CTE of 13 involves similar steps as the preparation of the previously mentioned molded members. The veneer ceramic powder was shaped by pressing. Subsequently, the molded members were preheated at 600° C. for 6 min. The molded members were heated at 730° C. in 15 min. During the heating, a vacuum was already applied. The maximum temperature was maintained for 2 min. The molded member was cooled in the furnace, wherein the door did not seal tightly, but was open a crack. Presintering at temperatures above 800° C. did not prove useful, since the densities of the thus obtained molded members were already too high for processing.

From the thus prepared molded members, veneers were ground in a commercially available CAD/CAM grinding system and then matched onto base metal caps. Before being scanned in, the Base metal scaffolds were treated with an opaquer to cover the dark intrinsic color of the metal. The dense-sintering was effected according to the following firing program:

preheat at 500° C. for 6 min heat at 880° C. with 55° C./min sinter to completion at 880° C. for 1 min The restoration was slowly cooled down in the furnace.

The temperature program employed corresponds to the normal firing program for this veneer ceramics.

FIGS. 3 and 4 show photographs of the composite of base metal scaffold and veneer ceramics.

The invention claimed is:

1. A dental restoration obtained by a process comprising the steps of molding together a first component and a second component to form a molded silicate-ceramic green body, wherein the second component has a different color than the first component, wherein the second component is arranged within the first component to form an interface in such a way that the interface represents a surface curved in space, and wherein the first and second components contain a feldspar ceramic material comprising feldspar and a metal oxide selected from the group consisting of $SiO_2$, $Al_2O_3$, $Na_2O$, and $K_2O$ or an oxide ceramic material comprising a metal oxide selected from the group consisting of $SiO_2$, $Al_2O_3$, and stabilized $ZrO_2$, partially sintering the molded silicate-ceramic green body to obtain a porous silicate-ceramic body having a first density and an ISO 6872 three-point bending strength of 25-180 MPa, milling the porous silicate-ceramic body to a silicate-ceramic precursor having the dental restoration shape, positioning the silicate-ceramic precursor directly on a ceramic scaffold or optionally opaquer-coated metal scaffold, and dense-sintering the silicate-ceramic precursor directly on, and fusing the precursor directly with, the ceramic scaffold or optionally opaquer-coated metal scaffold to obtain a silicate ceramic-fused final dental restoration having a second density such that the first-density/second-density ratio is 2/5-98/100.

2. The dental restoration of claim 1, wherein the molded silicate-ceramic green body has an ISO 6872 coefficient of thermal expansion (CTE) of at least $7 \times 10^{-6}$ $K^{-1}$.

3. The dental restoration of claim 1, wherein the molded silicate-ceramic en body has an ISO 6872 coefficient of thermal expansion of $7\text{-}18 \times 10^{-6}$ $K^{-1}$.

4. The dental restoration of claim 1, wherein the molded silicate-ceramic green body has an ISO 6872 coefficient of thermal expansion of $12\text{-}15 \times 10^{-6}$ $K^{-1}$.

5. The dental restoration of claim 1, wherein the molded silicate-ceramic green body has a holding element.

6. The dental restoration of claim 1, wherein the molded silicate-ceramic green body is embedded in a matrix.

7. The dental restoration of claim 1, wherein the step of milling the porous silicate ceramic body to a precursor having the dental restoration shape takes into account shrinkage occurring during subsequent dense sintering.

* * * * *